United States Patent [19]

Hirsch et al.

[11] Patent Number: 4,661,508
[45] Date of Patent: * Apr. 28, 1987

[54] AROMATASE INHIBITING α,α-DIPHENYL-4(5)IMIDAZOLE-METHANES OR -ETHANES

[75] Inventors: Kenneth S. Hirsch, New Palestine; Harold M. Taylor, Indianapolis, both of Ind.

[73] Assignee: Eli Lilly and Company, Indianapolis, Ind.

[*] Notice: The portion of the term of this patent subsequent to Aug. 12, 2003 has been disclaimed.

[21] Appl. No.: 732,535

[22] Filed: May 10, 1985

Related U.S. Application Data

[63] Continuation-in-part of Ser. No. 621,597, Jun. 18, 1984, abandoned.

[51] Int. Cl.$^4$ ................ A61K 31/415; C07D 231/12
[52] U.S. Cl. ................................. 514/396; 514/400; 548/335; 548/342; 548/345

[58] Field of Search ............... 548/342, 345, 335; 514/396, 400

[56] References Cited

U.S. PATENT DOCUMENTS

| | | | |
|---|---|---|---|
| 2,946,804 | 7/1960 | Zaugg et al. | 514/396 |
| 4,152,441 | 5/1979 | van der Stelt et al. | 514/400 |
| 4,213,994 | 7/1980 | Gebert et al. | 514/400 |
| 4,544,664 | 10/1985 | Karajalainen et al. | 514/396 |

FOREIGN PATENT DOCUMENTS 2101114  1/1983  United Kingdom ............ 548/335

Primary Examiner—Henry R. Jiles
Assistant Examiner—Kurt G. Briscoe
Attorney, Agent, or Firm—Robert A. Conrad; Leroy Whitaker

[57] ABSTRACT

This invention provides certain imidazole derivatives, their pharmaceutical formulations, and their use in a method of inhibiting aromatase and treating or preventing estrogen-dependent diseases in mammals.

20 Claims, No Drawings

AROMATASE INHIBITING α,α-DIPHENYL-4(5)IMIDAZOLE-METHANES OR -ETHANES This application is a continuation-in-part of application Ser. No. 621,597, filed June 18, 1984, now abandoned.

BACKGROUND OF THE INVENTION

Estrogens are synthesized from androgenic steroids. In the biosynthetic pathway for estrogen formation, aromatization is an essential step. It is generally believed that if the aromatase enzyme could be effectively inhibited, a useful treatment for estrogen dependent disorders could be obtained (see *Cancer Research*, Vol. 42, Suppl. 8:3261s (1982)).

Several estrogen dependent diseases exist which could be treated with aromatase inhibitors. These include breast cancer, endometriosis, polycystic ovarian disease, benign breast disease, and endometrial cancer. A beneficial effect of antiestrogens in the treatment of breast cancer has been well established (see *Br. J. Cancer*, 25, 270 (1971)). Two of the known aromatase inhibitors, testolactone and aminoglutethimide, have shown a beneficial effect in treatment of breast cancer. See *Cancer Research*, supra.

Endometriosis is characterized by an abnormal proliferation of the endometrium of the uterus. Since the endometrium is dependent on estradiol for its growth, an inhibitor of estrogen production should stop the progression of the disease.

Benign breast disease, or often called fibrocystic breast disease, appears to be dependent on ovarian steroids. See *Cancer*, 49, 2534 (1982). Aromatase inhibitors have not been tried in this disease, but antiestrogens seem to be of benefit. See *Obstet. Gynecol.*, 54, 80 (1979).

Polycystic ovarian disease is one of the most common causes of infertility in women. The disease appears to result from an abnormality in steroid metabolism, and the major form of therapy in this disease is the antiestrogen, clomiphene. See *Clin. Endocrinol.*, 12, 177 (1980).

It is the purpose of this invention to provide novel azole derivatives, their pharmaceutical formulations, and their use in a method for inhibiting the enzyme aromatase in mammals. The invention thus provides for the treatment or prevention of breast cancer and other estrogen-dependent diseases.

SUMMARY OF THE INVENTION

This invention provides imidazole derivatives of the formula

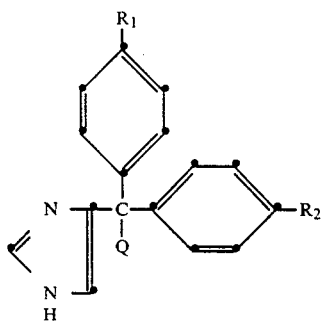

wherein

Q is hydrogen, hydroxy, halo, or methyl; and
$R_1$ and $R_2$ are independently halo or trifluoromethyl, or a pharmaceutically acceptable salt thereof.

In addition, this invention provides a method of inhibiting aromatase in mammals which comprises administering to said mammal an aromatase inhibiting amount of a compound of the above formula. By virtue of their ability to inhibit the enzyme aromatase, the compounds of the above formula are useful in the treatment and prevention of estrogen-dependent diseases, especially breast cancer, in mammals.

Further provided by this invention are pharmaceutical formulations comprising one or more of the compounds of the above formula in combination with a suitable pharmaceutical carrier, diluent, or excipient therefor. The formulations provided by this invention are particularly useful in treating mammals suffering from estrogen-dependent diseases such as breast cancer.

DETAILED DESCRIPTION AND PREFERRED EMBODIMENT

The term "halo" refers to fluoro, chloro, bromo, and iodo.

A preferred group of compounds useful in the method of this invention are those wherein:

(a) Q is hydrogen or hydroxy, and
(b) $R_1$ and $R_2$ are independently chloro, fluoro, or trifluoromethyl.

As will be recognized by those skilled in the art, many of the compounds used in this invention contain an asymmetric carbon atom. This invention is not limited to any particular isomer but includes the individual enantiomers as well as the racemates of the compounds.

Furthermore, it will be recognized that the compounds of the above formula, which are drawn as 4-substituted imidazoles, exist in equilibrium with the corresponding 5-substituted imidazole tautomers, and that reference to the compounds of this invention embodies both of these tautomers. The compounds are therefore referred to as 4(5)-substituted imidazoles.

The pharmaceutically acceptable acid addition salts used in this invention include salts derived from inorganic acids such as hydrochloric acid, nitric acid, phosphoric acid, sulfuric acid, hydrobromic acid, hydriodic acid, phosphorous acid and the like, as well as salts derived from organic acids such as aliphatic mono- and di-carboxylic acids, phenyl-substituted alkanoic acids, hydroxy-alkanoic and -alkanedioic acids, aromatic acids, aliphatic and aromatic sulfonic acids, and the like. Typical pharmaceutically acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate and the like salts. The preferred salts of this invention are those derived from inorganic acids, especially hydrochloric acid.

The compounds of this invention can be prepared by methods described in the art. The compounds employed in this invention are generically taught in British patent application GB No. 2,101,114; however, none of the presently claimed compounds are specifically disclosed. The presently claimed compounds can be prepared by the methods described in the British application. In addition, following the general procedure for making 2-substituted imidazoles as taught in U.S. Pat. No. 4,152,441, the following schemes summarize general methods to prepare the compounds of formula I wherein Q is hydrogen or hydroxy:

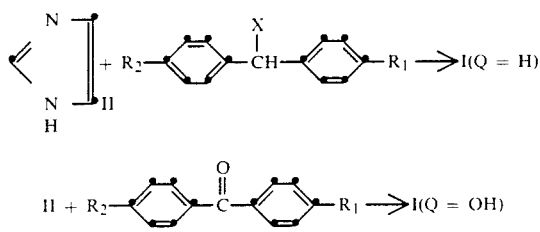

wherein X is chloro or bromo. According to the above schemes, imidazole (II) is treated with a strong alkali metal base, such as sodium hydride, n-butyllithium, or the like, in a non-reactive solvent, such as dimethylformamide, tetrahydrofuran, and the like. This reaction provides a mixture of the 1-, 2-, and 4-alkali metal derivatives of imidazole which is then reacted with the corresponding methyl halide or ketone derivative. The reaction is generally complete within 2-24 hours when the reaction is allowed to proceed at temperatures from about 0°-100° C. The reaction provides the corresponding derivatives of formula I wherein Q is hydrogen or hydroxy, together with the undesirable 1- and 2-substituted imidazoles. The isomeric materials may be isolated by known procedures, such as chromatography or crystallization.

An alternate procedure for preparing the carbinol derivatives of formula I is summarized by the following scheme:

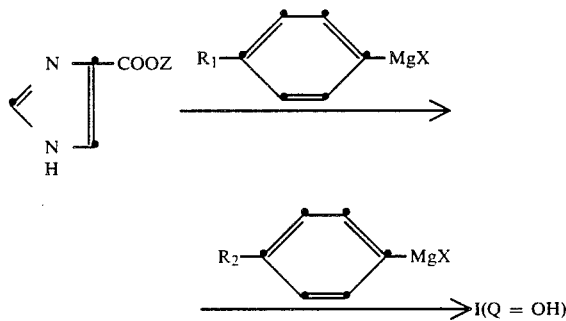

wherein Z is, for instance, $C_1$-$C_4$ alkyl, and X is chloro or bromo. In this procedure, an ester of 4-imidazole carboxylic acid is treated with the appropriate Grignard reagents following standard procedures. The reaction is generally carried out in a mutually compatible solvent, such as an ether, at temperatures from about $-20°$ to 60° C. This process is taught by Zaugg, et al. in *J. Org. Chem.*, 23, 847 (1958).

Other compounds of formula I can be prepared from the hydroxy and hydrogen compounds prepared by the above schemes. For instance, the halogen derivatives (I, Q=halo) are prepared from the corresponding hydrogen derivatives on treatment with an appropriate halogenating reagent, such as N-bromosuccinimide or N-chlorosuccinimide. The carbinol derivatives (Q is hydroxy) can also be prepared from the hydrogen compound by treating a basic solution of the hydrogen compound with air or oxygen. Conversely, the carbinol derivative may be transformed to the hydrogen compound following the procedure of U.S. Pat. No. 2,727,895. The methyl derivatives (I, Q is methyl) can be prepared from the corresponding compounds wherein Q is hydrogen by alkylation with a methyl halide following the general liquid ammonia/alkali metal amide procedure as described in U.S. Pat. No. 2,727,895.

In order to more fully illustrate the preparation of the compounds of this invention, the following examples are provided. The examples are illustrative only and are not intended to limit the scope of the invention in any way.

EXAMPLE 1

4(5)-[Bis(4-fluorophenyl)methyl]-1H-imidazole

Nine and two-tenths grams of sodium hydride (57% in oil) were added to a solution of 22 g of imidazole in 200 ml of dimethylformamide with stirring. When the reaction was complete as evidenced by cessation of foaming, 22 g of 4,4'-difluorodiphenylmethyl chloride were added with stirring. The mixture was stirred for 2 hours at room temperature and then warmed on a steam bath for 1.5 hours. The mixture was poured into an ice-water mixture, ether was added, and the layers were separated. The aqueous layer was washed with ether, and the combined ether extracts were washed with water, dried over magnesium sulfate, filtered, and evaporated. The residue was chromatographed over silica gel eluting successively with 10% ethyl acetate in toluene, 20% ethyl acetate in toluene, and 1:1 ethyl acetate/toluene (2 liters each mixture) to provide 1.2 g of 2-[bis(4-fluorophenyl)methyl]imidazole ($R_f$=0.44, silica gel TLC plates eluting with 1:1 ethyl acetate/toluene), 14.5 g of 1-[bis(4-fluorophenyl)methyl]imidazole ($R_f$=0.30), and 1.99 g of the desired 4(5)-[bis(4-fluorophenyl)methyl]imidazole ($R_f$=0.15). Structures were confirmed by NMR and infrared spectroscopy.

EXAMPLE 2

4(5)-[(4-Chlorophenyl)(4-fluorophenyl)methyl]imidazole

Following the general procedure of Example 1, the title compound was prepared from imidazole and 4-chlorophenyl-4-fluorophenylmethyl chloride in 3.1% yield.

EXAMPLE 3

α,α-bis(4-chlorophenyl)-4(5)-imidazolemethanol

A Grignard reagent was prepared from 4.7 g of magnesium turnings, a catalytic amount (four drops) of 1,2-dibromoethane in 2 ml of diethyl ether, and 25.0 g of 4-bromochlorobenzene in 100 ml of tetrahydrofuran. After stirring for approximately two hours, 5.0 g of methyl 4-imidazolecarboxylate were added as a solution in 50 ml of tetrahydrofuran. The mixture was heated at reflux for one hour. The tetrahydrofuran was removed by evaporation and the remaining mixture was poured into an iced ammonium chloride solution and extracted with ethyl acetate. Evaporation of the extract provided a yellow oil which was purified by chromatography over silica gel eluting with a gradient of ethyl acetate/15% methanol in ethyl acetate. The appropriate fractions were combined, evaporated, and crystallized from ethyl ether/hexane to provide 6.47 g of the title product. One gram of material was recrystallized from benzene to provide 540 mg of product with a melting point of 110°-113° C.

Analysis for $C_{16}H_{12}Cl_2N_2O$: Calculated: C, 60.41; H, 3.79; N, 8.78; Cl, 22.21. Found: C, 59.99; H, 4.03; N, 8.54; Cl, 22.29.

The compounds of this invention are useful in preventing or therapeutically treating estrogen-dependent diseases, including breast cancer, in mammals by virtue of their ability to inhibit the enzyme aromatase. Their ability to inhibit aromatase was demonstrated by employing a modification of the isolated rat ovarian microsome method of Brodie et al. in *J. Steroid Biochem.*, 7, 787 (1976). In this test system, ovarian microsomes are obtained from rats treated with pregnant mares serum gonadotropin. Test compounds are added to reaction vials containing 0.1 μM 4-androstene-3,17-dione, 100,000 dpm 1,2[$^3$H]-androstenedione, the microsomes and a NADPH generating system. The concentrations of the inhibitors tested ranged between 0.005 and 10 μM. In this assay, aromatization of androstenedione results in the production of [$^3$H]-$H_2O$ which is isolated by extracting the samples with chloroform and treating the aqueous phase with charcoal to remove the free steroid. Samples are counted in a liquid scintillation spectrometer and the percent inhibition determined by comparing the results with control samples incubated without inhibitor. Potency is determined based on the concentration of inhibitor in μM required to produce a 50% inhibition of enzyme activity ($EC_{50}$) when the concentration of substrate (androstenedione) is 0.1 μM. The $EC_{50}$'s of certain of the compounds of the above formula are summarized in Table 1.

TABLE 1

| Aromatase Inhibition in the Rat Ovarian Microsome Assay | |
|---|---|
| Compound of Example | $EC_{50}$* |
| 1 | <0.05 |
| 2 | <0.05 |
| 3 | <0.05 |

*Concentration of compound in μM required to achieve 50% inhibition of aromatase activity when substrate concentration is 0.1 μM.

By virtue of their ability to inhibit the enzyme aromatase, the compounds of this invention are able to inhibit the synthesis of estrogens in mammals, thereby making the compounds useful in the treatment of estrogen-dependent diseases, such as breast cancer. This activity was demonstrated in the following in vivo test system.

Estrogen Synthesis Inhibition in Rats

Immature female Wistar rats (45-55 grams) were divided into control and test groups of 4-5 animals each. Test compounds were administered for seven days daily by gavage in corn oil. Control animals received corn oil without the test compound. Beginning on the fourth day of the test, all animals treated with the test compound and one half of the control animals were given a subcutaneous injection of 1.0 mg of testosterone propionate in corn oil. The remaining control animals received only an equivalent volume of corn oil. On the seventh day of the test, rats treated with testosterone propionate were injected subcutaneously with 100 μCi of [$^3$H]-testosterone in 50 μl of 3:1 (v/v) saline-ethanol.

After two hours, the animals were killed by decapitation. Uteri were isolated, trimmed of extraneous connective tissue, and weighed. As summarized in Table 2 below, the corn oil treated animals exhibited low uterine weight and represent unstimulated or negative controls. In the control animals treated with testosterone propionate, estrogens produced by aromatization stimulated the uterus resulting in an increase in weight. Compounds which inhibit aromatization produced urerine weights significantly lower than those of the testosterone treated controls.

Ovaries from rats treated with [$^3$H]-testosterone were excised, cleaned of extraneous tissue, and homogenized in 2.5 ml of a 1.0 mM potassium phosphate buffer containing 3.0 mM $MgCl_26H_2O$, 320 mM sucrose, and 0.25% Triton X-100 (polyethylene glycol p-isooctyl phenyl ether, Rohm and Haas) at pH 6.5. The ovarian steroids were extracted with 1.5 ml of 9:1 (v/v) toluene/ethanol to which had been added 25 to 100 mcg each of unlabelled estradiol, estriol, and estrone, and approximately 1000 dpm of [$^{14}$C]-estradiol. The samples were vortexed, centrifuged at 500×g for 10 minutes, and the organic phase was transferred to a conical vial. Two additional extractions were performed on the residue in the same way. The pooled organic extracts were evaporated for subsequent thin-layer chromatography.

Ovarian proteins were precipitated by the addition of 5.0 ml of ethanol to the remaining aqueous phase. After an overnight incubation at 4° C., the samples were centrifuged at 1500×g for 10 minutes. The supernatant was discarded and the pellet was dissolved in 0.3N potassium hydroxide. Protein was determined according to the method of Bradford, *Analytical Biochemistry*, 72, 248 (1976).

The organic residue from each above extraction was redissolved in 9:1 (v/v) dichloromethane/methanol. The solution of each sample was applied to separate silica gel thin layer chromatography plates which contained a fluorescent indicator. The plates were developed in the first dimension with 160:38:1.5:0.5 (v/v/v/v) dichloromethane/ethyl acetate/methanol/acetic acid to within 3 cm of the top of the plate. After air-drying, the plate was developed in the second dimension with 180:19:1 (v/v/v) dichloromethane/methanol/ammonium hydroxide. The plate was air-dried and viewed under 254 nm UV light.

The visible spots were marked and the plates were sprayed with primulin (0.001% in 4:1 v/v acetone/water) according to the method of Wright, *J. Chromatography*, 59, 220 (1971) which allowed for the identification of additional steroids under 365 nm UV light. The spots were scraped from the plate using a glass wool plugged Pasteur pipet attached to a vacuum line. The steroids were eluted directly into scintillation vials by the addition of 0.2 ml of dichloromethane followed by two washes each of 2.0 ml of methanol. The organic solvent was evaporated and 10.0 ml of scintillation fluid (Beckman Ready Solv-NA) was added to the vials. Samples were analyzed by liquid scintillation spectrometry. Corrections were made based on the recoveries of the [$^{14}$C]-steroid. Steroid concentrations are expressed as femtomoles per milligram protein.

TABLE 2

| Effects of a Compound of Formula 1 on estrogen levels and uterine weight | | | | | | | |
|---|---|---|---|---|---|---|---|
| Test No. | Compound | Dose* | Animals | Mean Uterine Weight (mg) | Mean Steroid Concentration** | | |
| | | | | | estradiol | estrone | estriol |
| 1 | α,α-bis(4-chlorophenyl)-4(5)-imidazolemethanol | 1 | 5 | 214.2 | 0.35 | 0.00 | 0.132 |
| | | 3 | 5 | 158.8 ⁺ | 0.31 | 0.05 | 0.383 |
| | | 10 | 5 | 131.2 ⁺ | 0.19 ⁺ | 0.03 | 0.218 |
| | | 30 | 5 | 96.2 ⁺ | 0.22 | 0.07 | 0.391 |
| | | 100# | 4 | 79.5 ⁺ | 0.10 ⁺ | 0.36 ⁺ | 0.534 ⁺ |
| | Testosterone-treated control | — | 5 | 217.8 | 0.40 | 0.07 | 0.165 |
| | Corn oil control | — | 5 | 93.0 ⁺ | — | — | — |

*mg/kg p.o. by gavage
**femtomoles per milligram of protein.
⁺ significantly different from testosterone-treated control, $p < 0.05$.
evidence of toxicity was observed in this treatment group.

The compounds of this invention may be administered by any number of routes, including the oral, subcutaneous, intramuscular, intravenous, transdermal, and rectal routes. The compounds are usually employed in the form of pharmaceutical compositions. Such compositions are prepared in a manner well known in the pharmaceutical art and comprise from about 1 to about 95 percent by weight of at least one active compound of the above Formula I.

Such pharmaceutical compositions comprise as active ingredient a compound of the above formula associated with a pharmaceutically acceptable carrier. In making the compositions, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), ointments containing for example up to 10% by weight of the active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art.

For oral administration, a compound of this invention can be admixed with carriers and diluents molded into tablets or enclosed in gelatin capsules. The mixtures can alternatively be dissolved in liquids such as ten percent aqueous glucose solution, isotonic saline, sterile water, or the like, and administered intravenously or by injection. Such solutions can, if desired, be lyophilized and stored in a sterile ampoule ready for reconstitution by the addition of sterile water for ready intramuscular injection.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The active compounds are effective over a wide dosage range. For example, dosages per day will normally fall within the range of about 0.05 to about 300 mg/kg of body weight. In the treatment of adult humans, the range of about 0.1 to about 50 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way.

In order to more fully illustrate the operation of this invention, the following formulation examples are provided. The examples are illustrative only and are not intended to limit the scope of the invention. The formulations employ as active compounds any of the pharmaceutical compounds of the above formula.

EXAMPLE 4

Hard gelatin capsules are prepared using the following ingredients:

| | per capsule |
|---|---|
| 4(5)-[(4-fluorophenyl)(4-trifluoromethylphenyl)methyl]-imidazole | 250 mg |
| Starch dried | 200 mg |
| Magnesium stearate | 10 mg |
| Total | 460 mg |

The above ingredients are mixed and filled into hard gelatin capsules in 460 mg quantities.

EXAMPLE 5

Capsules each containing 20 mg of medicament are made as follows:

| | per capsule |
|---|---|
| 4(5)-[(4-chlorophenyl)(4-bromophenyl)methyl]imidazole | 20 mg |
| Starch | 89 mg |

-continued

|  | per capsule |
|---|---|
| Microcrystalline cellulose | 89 mg |
| Magnesium stearate | 2 mg |
| Total | 200 mg |

The active ingredient, cellulose, starch and magnesium stearate are blended, passed through a No. 45 mesh U.S. sieve and filled into hard gelatin capsules in 200 mg quantities.

EXAMPLE 6

Capsules each containing 100 mg of active ingredient are made as follows:

|  | per capsule |
|---|---|
| α,α-bis(4-chlorophenyl)-4(5)-imidazolemethanol | 100 mg |
| Polyoxyethylenesorbitan monooleate | 50 mcg |
| Starch powder | 250 mg |

The above ingredients are thoroughly mixed and are placed in an empty gelatin capsule.

EXAMPLE 7

Tablets each containing 10 mg of active ingredient are made up as follows:

|  | per tablet |
|---|---|
| 4(5)-[1,1-bis(4-trifluoromethylphenyl)ethyl]imidazole | 10 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 100 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 100 mg.

EXAMPLE 8

A tablet formula is prepared using the ingredients below:

|  | per tablet |
|---|---|
| 4(5)-[(4-chlorophenyl)(4-iodophenyl)chloromethyl]imidazole | 250 mg |
| Cellulose microcrystalline | 400 mg |
| Silicon dioxide fumed | 10 mg |
| Stearic acid | 5 mg |
| Total | 665 mg |

The components are blended and compressed to form tablets each weighing 665 mg.

EXAMPLE 9

Suppositories each containing 25 mg of active ingredient are made as follows:

|  | per suppository |
|---|---|
| α-(4-Bromophenyl)-α-(4-fluorophenyl)-4(5)-imidazolemethanol | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 10

Suspensions each containing 5 mg of medicament per 5 ml dose are made as follows:

|  | per 5 ml of suspension |
|---|---|
| 4(5)-[bis(4-fluorophenyl)bromomethyl]imidazole | 5 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethylcellulose and syrup to form a smooth paste. The benzoic acid solution, flavor and color is diluted with some of the water and added, with stirring. Sufficient water is then added to produce the required volume.

EXAMPLE 11

An aerosol solution is prepared containing the following components:

|  | Weight % |
|---|---|
| α-(4-chlorophenyl)-α-(4-trifluoromethylphenyl)-4(5)-imidazolemethanol | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted further with the remaining amount of propellant. The valve units are then fitted to the container.

We claim:

1. A compound of the formula

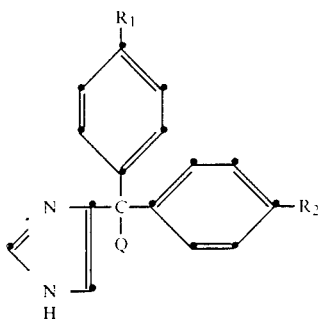

Q is hydrogen, hydroxy, halo, or methyl; and
R₁ and R₂ are independently halo or trifluoromethyl,
or a pharmaceutically acceptable salt thereof.

2. A compound of claim 1 wherein R₁ and R₂ are independently chloro, fluoro, or trifluoromethyl.

3. The compound of claim 2 which α,α-bis(4-chlorophenyl)-4(5)-imidazolemethanol or a pharmaceutically acceptable salt thereof.

4. The compound of claim 2 which is 4(5)-bis(4-fluorophenyl)methyl]imidazole or a pharmaceutically acceptable salt thereof.

5. A pharmaceutical composition useful to treat an estrogen-dependent disease which comprises an effective amount of a compound of claim 1 in combination with a suitable pharmaceutical carrier, diluent, or excipient therefor.

6. A composition according to claim 5 employing a compound wherein R₁ and R₂ are independently chloro, fluoro, or trifluoromethyl.

7. A composition according to claim 6 employing α,α-bis(4-chlorophenyl)-4(5)-imidazolemethanol or a pharmaceutically acceptable salt thereof.

8. A composition according to claim 6 employing 4(5)-[bis(4-fluorophenyl)methyl]imidazole or a pharmaceutically acceptable salt thereof.

9. A method of inhibiting aromatase in a mammal which comprises administering to said mammal an aromatase inhibiting amount of a compound of claim 1.

10. The method according to claim 9 employing a compound wherein R₁ and R₂ are independently chloro, fluoro, or trifluoromethyl.

11. The method according to claim 10 employing α,α-bis(4-chlorophenyl)-4(5)-imidazolemethanol as a pharmaceutically acceptable salt thereof.

12. The method according to claim 10 employing 4(5)-[bis(4-fluorophenyl)methyl]imidazole or a pharmaceutically acceptable salt thereof.

13. A method of treating estrogen-dependent diseases in a mammal which comprises administering to said mammal an effective amount of a compound of claim 1.

14. The method according to claim 13 employing a compound wherein R₁ and R₂ are independently chloro, fluoro, or trifluoromethyl.

15. The method according to claim 14 employing α,α-bis(4-chlorophenyl)-4(5)-imidazolemethanol or a pharmaceutically acceptable salt thereof.

16. The method according to claim 14 employing 4(5)-[bis(4-fluorophenyl)methyl]imidazole or a pharmaceutically acceptable salt thereof.

17. The method according to claim 13 wherein the estrogen-dependent disease is breast cancer.

18. The method according to claim 17 employing a compound wherein R₁ and R₂ are independently chloro, fluoro, or trifluoromethyl.

19. The method according to claim 18 employing α,α-bis(4-chlorophenyl)-4(5)-imidazolemethanol or a pharmaceutically acceptable salt therof.

20. The method according to claim 18 employing 4(5)-[bis(4-fluorophenyl)methyl]imidazole or a pharmaceutically acceptable salt thereof.

* * * * *